(12) United States Patent
Notté et al.

(10) Patent No.: US 9,777,027 B2
(45) Date of Patent: *Oct. 3, 2017

(54) METHOD FOR THE SYNTHESIS OF ETHANE-1-HYDROXY-1,1-DIPHOSPHONIC ACID

(71) Applicant: Straitmark Holding AG, Zug (CH)

(72) Inventors: Patrick Pierre Notté, Wavre (BE); Samuel Cogels, Brussels (BE)

(73) Assignee: STRAITMARK HOLDING AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/030,823

(22) PCT Filed: Oct. 24, 2014

(86) PCT No.: PCT/EP2014/072878
§ 371 (c)(1),
(2) Date: Apr. 20, 2016

(87) PCT Pub. No.: WO2015/059288
PCT Pub. Date: Apr. 30, 2015

(65) Prior Publication Data
US 2016/0264608 A1    Sep. 15, 2016

(30) Foreign Application Priority Data

Oct. 25, 2013    (EP) .................................... 13190248

(51) Int. Cl.
*C07F 9/38*    (2006.01)

(52) U.S. Cl.
CPC ............. *C07F 9/386* (2013.01); *Y02P 20/582* (2015.11)

(58) Field of Classification Search
None
See application file for complete search history.

(56) References Cited

U.S. PATENT DOCUMENTS 3,366,677 A    1/1968    Quimby
3,380,924 A    4/1968    Werdelmann
(Continued)

FOREIGN PATENT DOCUMENTS

DE    2343876    4/1974
DE    108511    9/1974
(Continued)

OTHER PUBLICATIONS

International Patent Application No. PCT/EP2014/072878, International Search Report and Written Opinion, dated Dec. 17, 2014, 11 pages.

*Primary Examiner* — Clinton Brooks
(74) *Attorney, Agent, or Firm* — Fitch, Even, Tabin & Flannery LLP

(57) ABSTRACT

The present invention is related to a method for the synthesis of ethane-1-hydroxy-1,1-diphosphonic acid or its salt which includes the steps of reacting tetraphosphorus hexaoxide and acetic acid under controlled reaction conditions; hydrolyzing the formed ethane-1-hydroxy-1,1-diphosphonic acid condensates to form ethane-1-hydroxy-1,1-diphosphonic acid; further processing the ethane-1-hydroxy-1,1-diphosphonic acid solution. The process according to the method of the present invention is highly controllable and further is characterized by a high selectivity.

17 Claims, 5 Drawing Sheets

(56) References Cited

U.S. PATENT DOCUMENTS

| | | | | |
|---|---|---|---|---|
| 3,400,147 A | * | 9/1968 | Rogovin | C07F 9/386 |
| | | | | 562/22 |
| 3,400,149 A | | 9/1968 | Quimby | |
| 3,471,406 A | * | 10/1969 | Budnick | C07F 9/3839 |
| | | | | 510/255 |
| 3,532,461 A | | 10/1970 | Whyte | |
| 3,959,360 A | | 5/1976 | Vazopolos | |
| 4,332,736 A | | 6/1982 | Starner | |
| 6,143,923 A | | 11/2000 | Shen | |

FOREIGN PATENT DOCUMENTS

| | | |
|---|---|---|
| DE | 2345199 | 9/1974 |
| DE | 214609 | 10/1984 |
| DE | 222600 | 5/1985 |
| EP | 0104974 | 4/1984 |
| GB | 981252 | 1/1965 |
| GB | 1131916 | 10/1968 |
| GB | 1138238 | 12/1968 |
| GB | 1145608 | 3/1969 |
| GB | 1398844 | 6/1975 |
| WO | 2009068636 | 6/2009 |
| WO | 2010055056 | 5/2010 |

* cited by examiner

EQUATION 1: P₄O₆ HYDROLYSIS

EQUATION 2: ACETYLPHOSPHITES FORMATION

EQUATION 3 : ACETYLPHOSPHONATE FORMATION

EQUATION 4: HEDP FORMATION

R = H OR AC

EQUATION 5/ HYDROLYSIS

METHOD FOR THE SYNTHESIS OF ETHANE-1-HYDROXY-1,1-DIPHOSPHONIC ACID

FIELD OF THE INVENTION

The present invention is related to a method for the synthesis of ethane-1-hydroxy-1,1-diphosphonic acid or its salts.

STATE OF THE ART

Ethane-1-hydroxy-1,1-diphosphonic acid and its salts are commonly used as scale and corrosion inhibitor in circulating cool water system, oil field and low-pressure boilers in fields such as electric power, chemical industry, industrial water treatment, metallurgy, fertilizer, etc. Ethane-1-hydroxy-1,1-diphosphonic acid or its salts also are added to detergents and other cleaning agents to prevent the effects of hard water. They are also used as peroxide stabilizer, dye-fixing agent and as chelating agent.

Various processes have been described for producing ethane-1-hydroxy-1,1-diphosphonic acid.

For example U.S. Pat. No. 3,400,147 discloses a process for the preparation of ethane-1-hydroxy-1,1-diphosphonic acid wherein phosphorous acid and acetic anhydride are reacted and wherein acetic acid is used as a solvent for the reaction.

DE 1072346 and U.S. Pat. No. 3,366,677 are related to a process for the preparation of ethane-1-hydroxy-1,1-diphosphonic acid wherein phosphorous acid, acetic anhydride and acetyl chloride are reacted.

GB 981,252, U.S. Pat. Nos. 3,959,360, 4,332,736 and 6,143,923 disclose a process wherein phosphorus trichloride is reacted with acetic acid.

The processes starting from either acetyl chloride or phosphorus trichloride, both suffer from the presence of acetyl chloride and/or hydrogen chloride present in the reaction medium as an initial reactant or produced during the manufacturing process. Extreme caution must be exercised in handling acetyl chloride because of its toxicity, volatility, combustibility, and reactivity with water and alkalis. Furthermore, because of the high reaction temperature, hydrogen chloride gas and unreacted acetyl chloride can leave the reactor.

DD 214609, GB 1,398,844, GB 1,145,608 and DE 2343876 disclose a process wherein acetic acid is reacted with phosphorus(III) oxide.

DD 214609 discloses a method for the manufacture of acyloxyalkane diphosphonic acid (reaction of alkane-1-hydroxy-1,1-diphosphonic acid and carboxylic acid) obtained from the reaction of a $C_2$ to $C_4$ carboxylic acid with $P_4O_{(6\ to\ 9)}$, wherein the molar ratio of $P_4O_{(6\ to\ 9)}$/carboxylic acid is 1/>10, at a temperature of less than 50° C. followed by maintaining the reaction mixture at a temperature between 90° C. and the boiling temperature of the carboxylic acid for a time period between 10 minutes and 3 hours.

GB 1,398,844 discloses a method for the production of ethane-1-hydroxy-1,1-diphosphonic acid which comprises reacting acetic anhydride and/or acetic acid with phosphorous acid and/or phosphorus trioxide respectively to form an acetylated intermediate product, adding water to the intermediate product in a portion not exceeding 1 mole of water per mole of phosphorus in the reaction mixture, heating the product sufficiently to distil glacial acetic acid therefrom and finally steam stripping the product. In this reference phosphorus trioxide is used as the phosphorus containing reagent, glacial acetic acid is used as the acetylating agent and only the reaction of acetic anhydride with phosphorous acid is illustrated.

GB 1145608 discloses a method for preparing ethane-1-hydroxy-1,1-diphosphonic acid which comprises the steps of 1) reacting an anhydride of phosphorous acid with a stoichiometric excess of acetic acid, in the absence of an organic solvent to form a reaction mixture containing phosphite intermediate compounds, 2) heating said reaction mixture to convert said phosphite intermediate compounds to compounds containing carbon atoms bonded directly to phosphorus atoms, and 3) treating the reaction mixture with water so as to hydrolyze said compounds, containing carbon atoms bonded directly to phosphorus atoms, to form ethane-1-hydroxy-1,1-diphosphonic acid.

DE 2343876 patent discloses a method for the simultaneous synthesis of alkane-1-hydroxy-1,1-diphosphonic acid (ethane-1-hydroxy-1,1-diphosphonic acid) and alkane carboxylic anhydride (acetic anhydride) through conversion of phosphor(III)-oxide and alkane carboxylic acid, characterized in that phosphor(III)-oxide, in a molar ratio to alkane carboxylic acids of less than 1:8, preferably 1:15, is converted into acylphosphites which, at a temperature ranging from 20° C. to the boiling temperature of the alkane carboxylic acid and preferably close to the boiling temperature, are further converted into alkane-1-hydroxy-1,1-diphosphonic acid condensates (ethane-1-hydroxy-1,1-diphosphonic acid) and alkane carboxylic anhydride (acetic anhydride); the alkane carboxylic acid and alkane carboxylic anhydride are distilled of under vacuum and the alkane-1-hydroxy-1,1-diphosphonic acid condensates are hydrolyzed.

In this patent it has been observed that for specified molar ratios of alkane carboxylic acid to tetraphosphorus hexaoxide the conversion into mono and di-acylphosphite happens, via an exothermic reaction, within a few minutes. The mono and di-acylphosphite in an homogeneous solution in the excess of carboxylic acid then are converted via another exothermic reaction into alkane-1-hydroxy-1,1-diphosphonic acid condensates and alkane carboxylic anhydride without that the reaction mixture becomes explosive.

The modus operandi as well as the reaction conditions presented in these patents, are such that the heat produced by the conversion of acetylphosphite and diacetylphosphite, accumulated in the reaction mixture, into acylphosphonate and its subsequent conversion to ethane-1-hydroxy-1,1-diphosphonic acid condensates (exothermic reaction) is difficult or even impossible to control as a result of which secondary products, which may be explosive, can be generated.

In order to control this highly exothermic conversion, solvents are introduced in GB 1131916 and U.S. Pat. No. 3,400,149 at the very beginning of the process in order to absorb some of the heat of the reaction. These solvents afterwards have to be separated and recovered, which makes these processes less attractive from an economical and ecological point of view.

GB 1131916 discloses a process for preparing ethane-1-hydroxy-1,1-diphosphonic acid comprising the steps of 1) reacting acetic acid with an anhydride of phosphorous acid, in the presence of an organic solvent which at least partially dissolves the said reactants and their reaction products and which has a boiling point of at least 140° C., to form a reaction mixture containing phosphite intermediate compounds, 2) heating said reaction mixture to convert said phosphite intermediate compounds to compounds containing carbon atoms bonded directly to phosphorus atoms, and 3) heating said reaction mixture with water so as to hydrolyze the said compounds containing carbon atoms bonded directly to phosphorus atoms to form ethane-1-hydroxy-1,1-diphosphonic acid.

U.S. Pat. No. 3,400,149 patent claims for a process for preparing ethane-1-hydroxy-1,1-diphosphonic acid which comprises the steps of adding $P_4O_6$ to acetic acid in the presence of an organic solvent, the molar ratio of $P_4O_6$ to acetic acid being in the range of from 1:1.5 to 1:50, respectively, thereby forming a reaction mixture containing phosphite intermediate compounds, heating said reaction mixture to a temperature in the range of from 90° C. to 150° C. for a minimum period of time of 3 minutes, thereby converting the phosphite intermediate compounds to phosphonate compounds and, thereafter adding water to hydrolyze said phosphonates to form a hydrolyzed solution of ethane-1-hydroxy-1,1-diphosphonic acid and free acetic acid. In an embodiment of the invention, the use of an excess acetic acid eliminates the need for another solvent or diluent for it serves satisfactorily as its own solvent as well as a solvent for the reaction intermediates.

It is disclosed that the reactants (acetic acid+$P_4O_6$) are brought together at about room temperature, whereupon they react very rapidly and form a great variety of intermediates. The phosphite anhydride intermediates, formed during the low temperature stages of the reaction start immediately and continue to rearrange as the temperature is being raised to a range of about 90° C. to about 150° C.; during this rearrangement the phosphite intermediates change to phosphonates. The temperature at which the phosphonate is formed rapidly is in the range of from about 90° C. to about 150° C. Below this temperature the conversion is relatively slow due, in part, to a gummy, viscous reaction mixture. Most of the examples as reproduced in the text indicate the formation of a gummy precipitate, which makes claimed method of preparation difficult for up-scaling.

DD 108511 patent claims for a method for the synthesis of ethane-1-hydroxy-1,1-diphosphonic acid from phosphorus(III)-oxide, phosphorous acid and an acetylating means consisting of acetic acid and/or acetic anhydride, characterized in that phosphorus(III)-oxide and phosphorous acid, in a molar ratio comprised between 10:1 and 1:10, preferably between 2:1 and 1:4 are mixed with the acetic acid and acetic anhydride, at a temperature between 80° C. and 120° C., preferable 115° C., in a period of time between 5 minutes and 4 hours, preferable 60 minutes and are converted, through the step of acetylphosphites, into partially condensed partially acetylated ethane-1-hydroxy-1,1-diphosphonic acids; the excess of acetylating means is removed by known methods and deacetylation, at temperatures comprised between 80° C. and 200° C. and at a vacuum between 1 mmHg and 250 mmHg results in ethane-1-hydroxy-1,1-diphosphonic acid condensates with recovering of acetylating means. The molar ratio of acetic acid to phosphor (III)-oxide compound is at least 2:1 while the molar ratio of acetic anhydride to phosphorous acid is at most 1.

According to DD 108551 the art comprises two main methods for the preparation of ethane-1-hydroxy-1,1-diphosphonic acid: first of all there is the method wherein phosphorus(III)-oxide and acetic acid are reacted to form simultaneously ethane-1-hydroxy-1,1-diphosphonic acid and acetic anhydride and wherein acetic anhydride has to be removed, for example by distillation, the acetic anhydride thus recovered being unusable as acetylating agent in a subsequent reaction; secondly there is the method wherein phosphorous acid with acetic anhydride are reacted to form simultaneously ethane-1-hydroxy-1,1-diphosphonic acid and acetic acid and wherein acetic acid has to be removed.

In the second method, most of the acetic anhydride, initially put into reaction with phosphorous acid, is hydrolyzed to acetic acid what is detrimental from an economical point of view. Besides, both methods each are characterized by the formation of considerable amounts of by-products.

The invention of DD 108511 is related to a method wherein the combined parallel use of phosphorus(III)-oxide and phosphorous acid, on the one hand and from acetic acid and acetic anhydride on the other hand allows for the preparation, in an exothermic reaction, of ethane-1-hydroxy-1,1-diphosphonic acid with a nearly 100% yield and substantially free of by-products.

As appears from the above, all processes reported in the art suffer from some disadvantages related either to economical aspects or to safety and environmental issues and without contesting the associated advantages of the state in the art processes, it nevertheless is obvious that there is still a need for a process which does not show any of the existing known drawbacks and/or shortcomings.

AIMS OF THE INVENTION

The present invention aims to provide a method for the synthesis of ethane-1-hydroxy-1,1-diphosphonic acid that does not present the drawbacks of the methods of the state of the art, especially a method that is more environmentally-friendly, economically attractive and safe.

SUMMARY OF THE INVENTION

The present invention discloses a method for the synthesis of ethane-1-hydroxy-1,1-diphosphonic acid or its salts, under controlled thermal conditions, by substantially avoiding the formation of phosphines and low oxides of phosphorus and the accumulation of phosphite intermediates, comprising the steps of:
a) forming a reaction mixture by gradually injecting tetraphosphorus hexaoxide, under optimal mixing conditions, below the surface of a liquid phase comprising acetic acid, while controlling the temperature of the reaction mixture in the range of from about 60° C. to about 200° C., wherein said reaction mixture comprises a molar ratio of acetic acid to tetraphosphorus hexaoxide comprised between about 4 and about 15, selected in such a way that the viscosity of the reaction mixture enables said optimal mixing conditions, the gradual injection leading to the formation of ethane-1-hydroxy-1,1-diphosphonic acid condensates,
b) hydrolyzing the ethane-1-hydroxy-1,1-diphosphonic acid condensates of the reaction mixture of step a) by adding water, wherein the molar ratio of water to tetraphosphorus hexaoxide, added in step a) is 2 or more, and maintaining the reaction mixture at a temperature comprised between about 100° C. and about 200° C. to obtain an aqueous solution comprising the ethane-1-hydroxy-1,1-diphosphonic acid.

Preferred embodiments of the present invention disclose one or more of the following features:
 the temperature range of the reaction mixture of step a) is achieved through an initial tetraphosphorus hexaoxide injection step or through a preheating of the liquid phase comprising acetic acid before starting the gradual injection of tetraphosphorus hexaoxide below the surface of said liquid phase;
 the reaction mixture of step a) is kept at a temperature of 60° C. or more, preferably of 80° C. or more for 5 minutes or more after the completion of the tetraphosphorus hexaoxide addition;

the viscosity of the reaction mixture of step a) is 10 Pa·s or less, preferably 8 Pa·s or less, more preferably 6 Pa·s or less and most preferably 5 Pa·s or less, as measured by an "in process" vibrational viscometer calibrated with Certified Standard Oils, at the temperature of the reaction mixture, comprised between about 60° C. and about 200° C., throughout the complete duration of step a);

the liquid phase comprising acetic acid comprises water, forming an aqueous solution of acetic acid, wherein the molar ratio of water of said aqueous solution to the total amount of tetraphosphorus hexaoxide, added in step a) is comprised between about 0.007 and about 3.0, preferably between about 0.1 and about 2.0 and more preferably between about 1.0 and about 1.5;

the method of the present invention further comprises the steps of:
  distilling the excess of acetic acid from the aqueous solution of step b) and adjusting the water content to obtain an aqueous solution comprising ethane-1-hydroxy-1,1-diphosphonic acid, or
  cooling the aqueous solution of step b) to obtain a precipitate of ethane-1-hydroxy-1,1-diphosphonic acid and optionally isolating the precipitate to obtain solid ethane-1-hydroxy-1,1-diphosphonic acid;

the method of the present invention further comprises the step of neutralizing ethane-1-hydroxy-1,1-diphosphonic acid through the addition of a base selected from the group consisting of hydroxides of alkali metals, hydroxides of alkaline earth metals, ammonia and amines, to form the corresponding salt;

the molar ratio of acetic acid to the total amount of tetraphosphorus hexaoxide added in step a) is comprised between about 4 and about 15 and preferably between about 5 and about 10;

in step a) the tetraphosphorus hexaoxide is gradually injected in the liquid phase (below the surface) of acetic acid or of the aqueous solution of acetic acid for a period of time comprised between about 5 minutes and about 5 hours;

the reaction mixture of step a) is heated to a temperature comprised between about 60° C. and about 200° C., preferably between about 80° C. and about 160° C. and more preferably between about 100° C. and about 140° C. and is maintained at that temperature throughout the tetraphosphorus hexaoxide addition step;

the reaction mixture of step a) is maintained at a temperature comprised between about 90° C. and about 200° C., preferably between about 100° C. and about 160° C. and more preferably between about 100° C. and about 130° C. for a period of time comprised between about 5 minutes and about 2 hours after the completion of the tetraphosphorus hexaoxide addition;

the molar ratio of water added in step b) to the total amount of tetraphosphorus hexaoxide added in step a) is between about 2 and about 6, preferably between about 3 and about 6, more preferably between about 4 and about 5.5 and most preferably about 4.5;

step b) is maintained at a temperature comprised between about 100° C. and about 170° C., preferably between about 130° C. and about 150° C. for a period of time comprised between about 5 minutes and about 4 hours;

the excess of acetic acid is distilled in step b) by steam injection;

the aqueous solution of step b) is cooled to a temperature comprised between about 15° C. and about 40° C. to form a precipitate of ethane-1-hydroxy-1,1-diphosphonic acid;

the excess of acetic acid is recovered and reused preferably in step a) and step b) of the method;

the ethane-1-hydroxy-1,1-diphosphonic acid is obtained in a batch process;

ethane-1-hydroxy-1,1-diphosphonic acid, obtained by the method of the present invention, is used for the preparation of its sodium, potassium or ammonium salt;

ethane-1-hydroxy-1,1-diphosphonic acid or its salts, obtained by the method of the present invention, are used as scale inhibitor, corrosion inhibitor, dispersing agent and/or sequestering agent.

BRIEF DESCRIPTION OF THE DRAWINGS

In FIG. 3, (1) represents the stirrer shaft with three sets of four blades, (2) represents the reactor wall, (3) represents the tetraphosphorus hexaoxide injection tubing, (4) represents the baffles and (5) represents the reaction medium.

equation 4 represents the formation of ethane-1-hydroxy-1,1-diphosphonic acid condensates through reaction of acyl phosphonate with phosphorous acid.

equation 5 represents the formation of ethane-1-hydroxy-1,1-diphosphonic acid through hydrolysis of the ethane-1-hydroxy-1,1-diphosphonic acid condensates, of ethane-1-acetyl-1,1-diphosphonic acid and of the dimers of ethane-1-hydroxy-1,1-diphosphonic acid.

Figure 5:
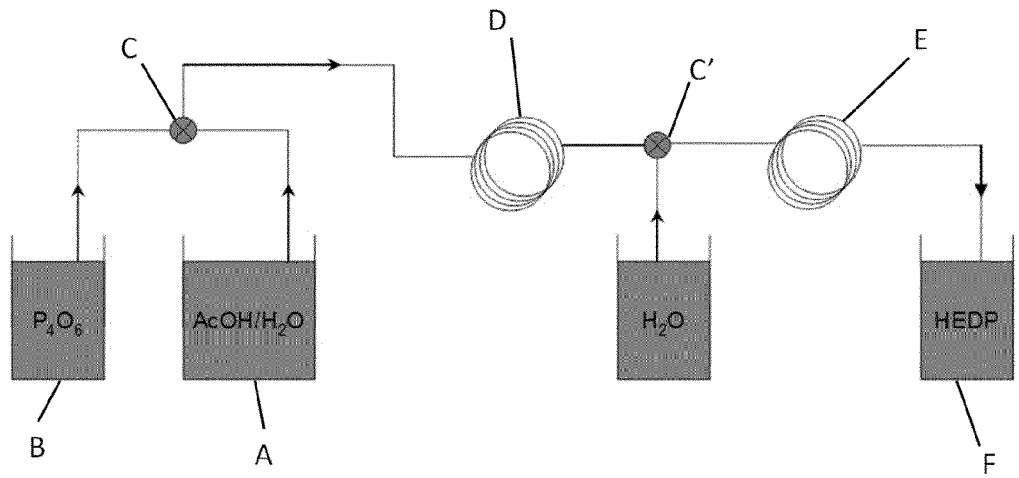

FIG. 5 represents the system employed for the continuous synthesis of 1-hydroxyethane-1,1-diphosphonic acid wherein (A) represents the vessel containing acetic acid and optionally water, (B) represents the vessel containing tetraphosphorus hexaoxide, (C) represents the mixing unit for mixing the acetic acid, optionally comprising water, and tetraphosphorus hexaoxide, (D) represents the reactor where ethane-1-hydroxy-1,1-diphosphonic acid condensates are formed, (C') represents the mixing unit for mixing ethane-1-hydroxy-1,1-diphosphonic acid condensates and water, (E) represents the reactor where ethane-1-hydroxy-1,1-diphosphonic acid condensates are hydrolysed and ethane-1-hydroxy-1,1-diphosphonic acid is formed and (F) represents the unit where ethane-1-hydroxy-1,1-diphosphonic acid is further processed i.e. distilling of unreacted acetic acid and adjusting the water content of the aqueous solution of ethane-1-hydroxy-1,1-diphosphonic acid or, cooling down the aqueous solution, comprising the unreacted acetic acid, whereupon a precipitate of ethane-1-hydroxy-1,1-diphosphonic acid is formed and isolating the precipitate through filtration.

On lab-scale the system is composed of three HPLC pumps (respectively connected to vessel (A), (B) and a vessel containing water), 1 mm bore PFA tubings, T type mixers (C) and (C'), two heated coil reactors (D) and (E) composed of 1 mm bore tubing made of stainless steel and with an internal volume of 10 ml.

Figure 6:
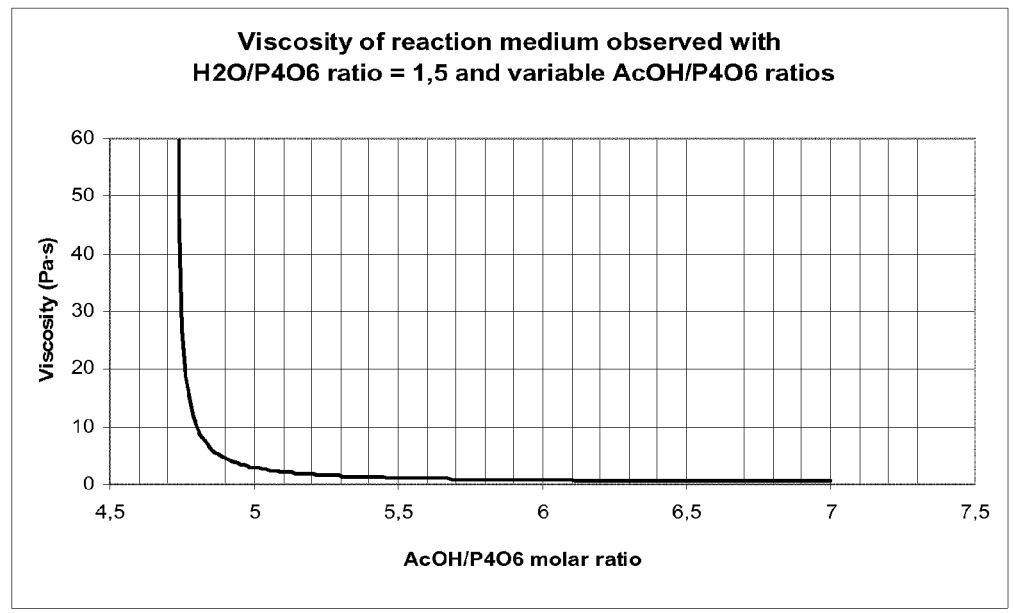

FIG. 6 represents a graph showing the dynamic viscosity as a function of the acetic acid/tetraphosphorus hexaoxide molar ratio for a reaction mixture with a constant water/tetraphosphorus hexaoxide molar ratio of 1.5.

DETAILED DESCRIPTION OF THE INVENTION

The present invention provides an improved method (that is safe, economical and environmental friendly) for the synthesis of ethane-1-hydroxy-1,1-diphosphonic acid.

The method includes the steps of:
reacting tetraphosphorus hexaoxide and acetic acid, the tetraphosphorus hexaoxide being gradually injected in the liquid phase, for example below the surface of acetic acid in a batch mode process or, in a stream of acetic acid in a continuous process, while controlling the temperature at a value of about 60° C. or more, preferably at a value comprised between about 80° C. and about 200° C.;
hydrolyzing the formed hydroxy-diphosphonic acid condensates to form an aqueous solution comprising ethane-1-hydroxy-1,1-diphosphonic acid with a yield of preferably at least 50%, more preferably at least 70% and most preferably at least 90%;
further processing said aqueous solution through adjusting the water and acetic acid contents of said solution and/or through cooling down said solution and filtering the solid ethane-1-hydroxy-1,1-diphosphonic acid precipitate thus obtained.

The tetraphosphorus hexaoxide used within the scope of the present invention may be represented by a substantially pure compound containing at least 85%, preferably more than 90%, more preferably at least 95% and in one particular execution at least 97% of $P_4O_6$. While tetraphosphorus hexaoxide, suitable for use within the context of this invention, may be manufactured by any known technology, in preferred executions it is prepared in accordance with the method described in WO 2009/068636 and/or WO 2010/055056 under the section entitled "Process for the manufacture of $P_4O_6$ with improved yield". This section is hereby incorporated by reference. In detail, oxygen, or a mixture of oxygen and inert gas, and gaseous or liquid phosphorus are reacted in essentially stoichiometric amounts in a reaction unit at a temperature in the range from about 1600 to about 2000 K, by removing the heat created by the exothermic reaction of phosphorus and oxygen, while maintaining a preferred residence time of from about 0.5 to about 60 seconds followed by quenching the reaction product at a temperature below 700 K and refining the crude reaction product by distillation. The tetraphosphorus hexaoxide so prepared is a pure product containing usually at least 97% of the oxide. The so produced $P_4O_6$ is generally represented by a liquid material of high purity containing in particular low levels of elementary phosphorus, $P_4$, preferably below 1000 ppm, expressed in relation to the $P_4O_6$ being 100%. The preferred residence time is from about 5 to about 30 seconds, more preferably from about 8 to about 30 seconds. The reaction product can, in one preferred execution, be quenched to a temperature below 350 K.

It is presumed that the $P_4O_6$ participating in a reaction at a temperature of from 24° C. (melting t°) to 200° C. is necessarily liquid or gaseous although solid species can, academically speaking, be used in the preparation of the reaction medium.

For reasons of convenience and operational expertise, the tetraphosphorus hexaoxide, represented by $P_4O_6$, is of high purity containing very low levels of impurities, in particular elemental phosphorus, $P_4$, at a level below 1000 ppm, usually below 500 ppm and preferably not more than 200 ppm, expressed in relation to the $P_4O_6$ being 100%.

The acetic acid used within the scope of the present invention may be anhydrous acetic acid, for example obtained through the addition of acetic anhydride to acetic acid comprising a minor quantity of water; otherwise, the acetic acid used within the scope of the present invention, may be mixture of acetic acid and water.

In a preferred embodiment of the present invention the acetic acid is used as a mixture comprising water, the aqueous solution of acetic acid being characterised by a water content of from about 0.05% to about 23% by weight. It is well know that such a concentration range includes glacial acetic acid as well as aqueous solutions of acetic acid. The aqueous solution of acetic acid terminology is aimed at comprising the entire range of water content. The aqueous solution of acetic acid used within the scope of the present invention optionally is glacial acetic acid.

The process of the present invention is started by charging acetic acid, preferably an aqueous solution of acetic acid into a reactor. Tetraphosphorus hexaoxide is gradually injected in the liquid phase (below the surface) of the acetic acid, preferably in the liquid phase (below the surface) of the aqueous acetic acid solution.

For the case of an aqueous solution of acetic acid, the gradual injection of tetraphosphorus hexaoxide results in an immediate and continuous increase of the temperature of the reaction mixture until a fixed preset temperature between about 60° C. and about 200° C., is obtained.

For the case of anhydrous acetic acid, the anhydrous acetic acid is preferably heated up to a temperature comprised between about 60° C. and about 200° C. before the start of the tetraphosphorus hexaoxide addition.

Intermediary cases are possible dependent on the amount of water initially present in the aqueous acetic acid solution.

Once the temperature has reached its preset value, comprised between about 60° C. and 200° C., preferably between about 80° C. and about 160° C., more preferably between about 100° C. and about 140° C. and most preferably between about 100° C. and about 130° C., it is maintained at that preset value throughout the remaining tetraphosphorus hexaoxide injection step by monitoring and adjusting the injection rate of the tetraphosphorus hexaoxide. The injection rate of the tetraphosphorus hexaoxide is dependent on the capabilities of the reactor's heat exchanging means for managing and controlling the heat generated by the reaction.

Though some of the reactants of step a) may be thermally unstable at temperatures above about 160° C., when they are considered as such, it is believed that these reactants under specific reaction conditions are instantly converted into products which are more stable at these elevated temperatures.

The upper temperature limit actually aims at preventing any substantially undue thermal decomposition of the tetraphosphorus hexaoxide and of the products formed during the reaction. It is understood and well known that the decomposition temperatures can vary depending upon additional physical parameters, such as pressure and the co-reactants in the reaction mixture.

Preferably, the quantity of acetic acid is such that the molar ratio of acetic acid to the total amount of tetraphosphorus hexaoxide to be added to the solution comprising acetic acid is between 4 and 15 and preferably between 5 and 10.

Preferably, the quantity of water present in the aqueous solution of acetic acid, preferably used in the method of the present invention, is such that the molar ratio of water, present in the solution, to the total amount of tetraphosphorus hexaoxide to be injected to said solution is at most 4, preferably between about 0.007 and about 3.0, more preferably between about 0.1 and about 2.0 and most preferably between about 1.0 and about 1.5.

Preferably, the gradual injection of the tetraphosphorus hexaoxide is performed over a period of between about 5 minutes and about 5 hours in such a way that the temperature of the reaction mixture remains within a predefined manageable range.

The gradual injection of the tetraphosphorus hexaoxide is performed under optimal mixing conditions which are for example obtained under intensive stirring. Optimal mixing conditions are obtained when the reaction characteristics are not sensitive to addition rate fluctuations of the reactants, i.e. when there is an almost immediate homogeneous distribution of the reactants throughout the reaction medium. The optimal mixing conditions are intended to have a substantial constant temperature during the entire tetraphosphorus hexaoxide injection step. Typical mixing equipment is well known by those skilled in the art and is for example a stirrer equipped with axial or radial flow impellers, a static mixer or an ultrasonic mixer, used as a single or combined equipment.

Optimal mixing conditions are obtained for a reaction medium characterized by an adequate viscosity. By an adequate viscosity, it is meant, within the scope of the present invention, a dynamic viscosity of 10 Pa·s or less, preferably of 8 Pa·s or less, more preferably of 6 Pa·s or less and most preferably of 5 Pa·s or less, measured at the temperature of the reaction mixture of step a), throughout the complete temperature range of step a), and throughout the whole duration of step a) i.e. from the initiation of the $P_4O_6$ injection till completion of step a).

The dynamic viscosity values, as specified within the scope of the present invention are these as obtained from the ReactaVisc 300 "in process" vibrational viscometer from Hydramotion Ltd., calibrated with Cannon Certified Standard Oils which are traceable to the National Institute of Standards and Technology.

The use of a mixture of acetic acid and water in step a) may be intended for adjusting the viscosity of the reaction mixture throughout step a) within specific limits enabling optimal mixing. The molar ratio's of acetic acid to $P_4O_6$ and of water to $P_4O_6$ will determine the viscosity throughout step a); in order to obtain and maintain appropriate reaction conditions, the selection of specific experimental ratio's, within the respective ranges, as claimed in the present invention, is obvious for those skilled in the art.

It is very important that the reaction mixture is adequately stirred throughout the reaction zone. If stirring is inadequate, mixing conditions decrease, as a result of which the desired reaction rate is adversely affected and, in addition, undesirable by-products may be formed.

The rate of the gradual injection of tetraphosphorus hexaoxide, the intensity of the stirring, the temperature throughout the addition of tetraphosphorus hexaoxide as well as the fact that tetraphosphorus hexaoxide is injected below the surface of the acetic acid or preferably the aqueous solution of acetic acid of step a) are critical parameters for controlling the exothermic reaction, preventing any substantial undue decomposition of the reactants or of the intermediates formed in these reactions and avoiding the formation of highly unstable LOOPs (Low Oxide of Phosphorus), As disclosed in "Phosphorus compounds", Kirk-Othmer encyclopaedia Vol. 18 page 737-799 and by J. G. Riess and J. R. Van Wazer in "The Descriptive Chemistry of Phosphorus Trioxide", Inorg. Chem. February 1966, Vol. 5, No 2, pages 178-183, LOOPs, which form a yellow to yellow-orange solid, are a complex mixture of lower oxides and polymers of phosphorous. LOOPs may either hydrolyse slowly, be pyrophoric or pyrolyze rapidly and yield toxic, flammable, self-igniting and explosive diphosphine-contaminated phosphines. LOOPs can also decompose explosively in the presence of moisture and air near about 150° C.

The presence of LOOPs in a reactor system thus represents a considerable safety hazard: an explosion can result from the presence of LOOPs. Therefore, today's industrial synthesis processes of ethane-1-hydroxy-1,1-diphosphonic acid require to control for LOOPs and to make provision for the case that LOOPs are detected. The control for LOOPs is highly important for reaction temperatures above 120° C. and above all, before the onset of the hydrolysis step b).

The inventors have perceived that the gradual addition of tetraphosphorus hexaoxide to acetic acid or to an acetic acid aqueous solution, whereby the addition is done above the surface of the liquid phase, which is a general accepted way of performance, even for said addition being performed at a temperature comprised between about 60° C. and about 200° C. and under intensive stirring conditions, the formation of LOOPs and phosphines cannot be prevented.

Without wishing being bond by theory it is believed that the reaction of tetraphosphorus hexaoxide with acetic acid in the vapor phase above the liquid phase of acetic acid or the aqueous acetic acid solution, and the possible subsequent reactions of possible intermediates within this vapor phase are the cause of this LOOP and phosphine formation.

The inventors now have surprisingly found that the gradual injection of tetraphosphorus hexaoxide in the liquid phase, i.e. below the surface of the liquid phase, comprising acetic acid is mandatory for avoiding the formation of LOOPs and phosphines, even for optimal mixing conditions at mixing temperatures comprised between about 60° C. and about 200° C. being fulfilled.

Figure 4:
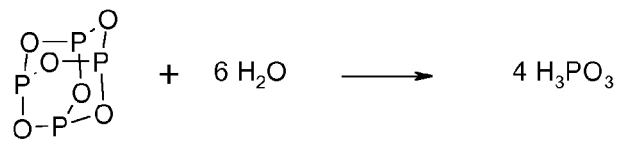
FIG. 4 shows some examples of possible reactions involved in the synthesis of ethane-1-hydroxy-1,1-diphosphonic acid from an acetic acid/water mixture and tetraphosphorus hexaoxide. In this figure,
  equation 1 represents the conversion of the tetraphosphorus hexaoxide into phosphorous acid through the reaction of tetraphosphorus hexaoxide and water of the aqueous acetic acid solution;
  equation 2 represents the formation of acyl phosphite and (di) acyl phosphite through the reaction of tetraphosphorus hexaoxide and acetic acid;
  equation 3 represents the formation of acyl phosphonate through the reaction of acylphosphite or (di)acyl phosphite with phosphorous acid.
Figure 4:
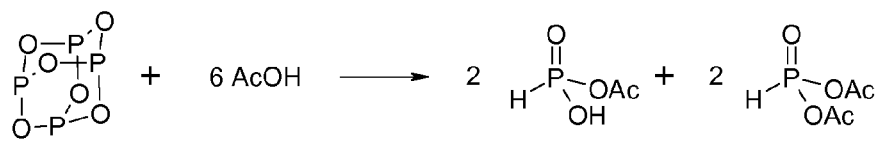
Figure 4:
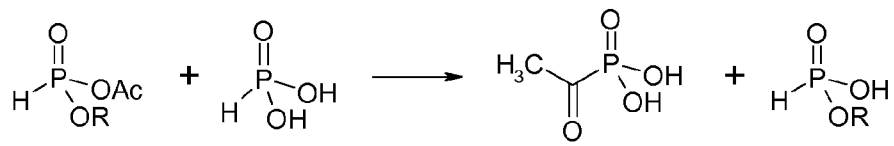
Figure 4:
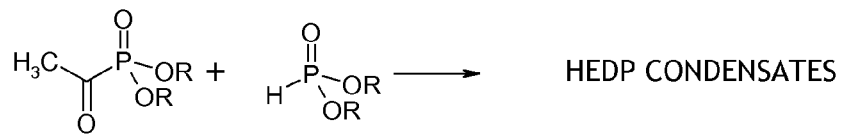
Figure 4:
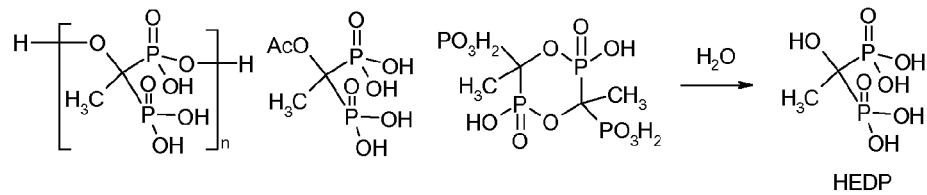

At the onset of the tetraphosphorus hexaoxide addition, the water, preferably present in the acetic acid of step a) converts part of the tetraphosphorus hexaoxide into phosphorous acid (FIG. 4 Equation 1). The hydrolysis of tetraphosphorus hexaoxide is exothermic generating about 300 kJ per mole of tetraphosphorus hexaoxide. The exotherm resulting from the tetraphosphorus hexaoxide hydrolysis and from the reaction of tetraphosphorus hexaoxide with acetic acid, leading to acyl phosphite and diacyl phosphite, along with the energy management from external heating sources is used to bring the reaction mixture to a preset temperature comprised between about 60° C. and about 200° C., preferably between about 80° C. and about 160° C., more preferable between about 100° C. and about 140° C. and most preferable between about 100° C. and about 130° C. within the initial phase of the tetraphosphorus hexaoxide injection and, after the initial temperature increase obtained within said initial phase, to maintain the reaction mixture at that preset temperature throughout the further injection of the remaining tetraphosphorus hexaoxide.

The substantial constant preset temperature of about 60° C. or more and the thoroughly stirring are key parameters for a continuous conversion of:
tetraphosphorus hexaoxide and acetic acid into acyl phosphite and (di)acyl phosphite, (FIG. 4, Equation 2)
acyl phosphite and (di)acyl phosphite into acylphosphonate (FIG. 4, Equation 3),
acylphosphonate, acyl phosphite and/or (di)acyl phosphite through reaction with phosphorous acid into ethane-1-hydroxy-1,1-diphosphonic acid condensates, (FIG. 4, Equation 4)
essentially throughout the entire tetraphosphorus hexaoxide addition of step a). The above intermediate reactions are presumed to be one of the multiple possibilities for obtaining ethane-1-hydroxy-1,1-diphosphonic acid.

For step a) standing at a temperature below 60° C., the reaction substantially will stop at the stage of acyl phosphite and diacyl phosphite, which will accumulate in the reaction mixture of step a). Increasing the temperature of the reaction mixture above about 60° C., after the completion of the tetraphosphorus hexaoxide addition, will initiate the instantaneous conversion of acyl phosphite and diacyl phosphite into acylphosphonate and ultimately into the ethane-1-hydroxy-1,1-diphosphonic acid condensates which are very exothermic reactions impossible to control. On industrial scale this would generate a major danger.

For step a) standing at a temperature comprised between 60° C. and 200° C. but performed by adding tetraphosphorus hexaoxide above the surface of the liquid phase comprising acetic acid, significant quantities of LOOPs and phosphines will be formed rendering the process unsafe.

After the completion of the tetraphosphorus hexaoxide addition in step a), the reaction mixture is heated to a temperature of about 90° C. or more, preferably to a temperature between about 90° C. and about 200° C., more preferably between about 100° C. and about 160° C. and most preferably between about 100° C. and about 130° C. for a period of time comprised between about 5 minutes and about 2 hours, preferably for a period of time of about 30 minutes to complete the conversion into ethane-1-hydroxy-1,1-diphosphonic acid condensates. During this period of time part of the excess of not reacted acetic acid, initially added, may be distilled off.

In step b) water is added to the reaction mixture of step a) in order to hydrolyze the ethane-1-hydroxy-1,1-diphosphonic acid condensates. The condensates are dimers and polymers wherein the ethane-1-hydroxy-1,1-diphosphonic acid units are linked at least partially through P—O—P-anhydride bonds and P—O—C ester bonds.

The molar ratio of the water added in step b) to the tetraphosphorus hexaoxide added in step a) is at least about 2, preferably comprised between about 3 and about 6, more preferably between about 4 and about 5.5 and most preferably about 4.5.

If the molar ratio is less than 2, precipitation of the reaction mixture or even complete solidification will most probably appear, making the process conditions difficult to manage. The solidification of the reaction mixture hinders adequate stirring as a result of which hydrolysis of the ethane-1-hydroxy-1,1-diphosphonic acid condensates and consequently the further processing is almost stopped. Therefore the best process conditions are attained for a molar ratio higher than about 4.

The temperature of step b) is comprised between about 100° C. and about 170° C. and preferably between about 130° C. and about 150° C. for a period of time comprised between about 5 minutes and about 4 hours. The exotherm produced by the hydrolysis of the ethane-1-hydroxy-1,1-diphosphonic acid condensates in step b) as well as the supply of heat from an external source may be used to induce the distillation of the remaining acetic acid excess present in the reaction mixture.

The distillation of acetic acid in step b) can be supported by a steam injection. The amount of steam used in this step is comprised between about 5% and about 40% of the total amount of compounds added in step a) and step b). The steam injection is preferably performed at a temperature comprised between about 100° C. and about 170° C., preferably between about 130° C. and about 150° C. for a preferred period of time comprised between about 5 minutes and about 4 hours.

The acetic acid collected from step a) and from step b) can be reused when accomplishing a subsequent process according to the method of the present invention.

The method of the present invention thus presents considerable economical and environmental benefits not only because it is characterized by a high yield and selectivity, but also because of the substantially 100% recovery and reuse of the unreacted reactants without any purification.

Since the molar ratios of acetic acid, tetraphosphorus hexaoxide and water in step a), are essential criteria for the method of the present invention to be successful, the water content of the excess acetic acid, distilled from the aqueous solution of step a) and step b) is important to be known and not to exceed specific limits in order to be reused, with good results, in a subsequent process.

In order to meet commercial application specifications, low levels of acetic acid in the final product are required; therefore the amount of injected steam is adjusted as a result of which the amount of water present in the distilled acetic acid may be too high for direct reuse without passing through a purification step. In order to avoid any waste or purification step, it may be advantageous to split the distillate in two distinct fractions. The first fraction will contain the amount of water as defined for step a), and the second fraction, which contains a higher amount of water, may be used, as a partial substitute for pure water, in step b). This arrangement offers a better flexibility to reach low levels of acetic acid in the end product while recycling all recovered acetic acid in the subsequent process operation.

The end product of the method of the present invention is either an aqueous solution of ethane-1-hydroxy-1,1-diphosphonic acid at a specific concentration or solid ethane-1-hydroxy-1,1-diphosphonic acid.

When the end product is a solid, no distillation of acetic acid is required. On the contrary, it has been observed that the presence of acetic acid has a positive effect on the precipitation upon cooling the aqueous solution of step b).

The aqueous solution of ethane-1-hydroxy-1,1-diphosphonic acid meeting a specific concentration of ethane-1-hydroxy-1,1-diphosphonic acid is obtained by adjusting the water content of the aqueous solution of step b) either through the addition of water or through distilling off a certain amount of excess of water. In general the aqueous solution of ethane-1-hydroxy-1,1-diphosphonic acid, obtained in step b) is stable at temperatures of about 100° C. and above; once cooling down the aqueous solution of step b), ethane-1-hydroxy-1,1-diphosphonic acid will crystallize. Therefore in order to have aqueous solutions of ethane-1-hydroxy-1,1-diphosphonic acid which are stable at ambient temperature and below, i.e. in normal use and shipping conditions, the aqueous solutions of step b) generally are adjusted for their water content through addition of water.

Solid ethane-1-hydroxy-1,1-diphosphonic acid is obtained through cooling down of the aqueous solution of step b) upon which a precipitate of ethane-1-hydroxy-1,1-diphosphonic acid is formed. The precipitate then is filtered using conventional filtration techniques as known in the art.

The aqueous solution of step b) is cooled down to a temperature comprised between about 15° C. and about 40° C. and preferably between about 20° C. and about 25° C. Alternatively, before cooling down the aqueous solution, it first can be concentrated through distilling off a preset amount of water whereupon the concentrated solution is cooled down bringing about crystallization of ethane-1-hydroxy-1,1-diphosphonic acid, preferably as a monohydrate. The presence of acetic acid in the aqueous solution of step b) is key for the crystallization to happen.

For practical reasons, it may be important to control the amount of residual acetic acid in the end product and to keep it below a maximum value which is specified by the final use of said product. Purification of the end product then may be required. If the final product is an aqueous solution of ethane-1-hydroxy-1,1-diphosphonic acid the purification is obtained by steam injection. Otherwise, if the end product is a solid the purification may be obtained by washing the ethane-1-hydroxy-1,1-diphosphonic acid crystals with a controlled amount of water.

The method according to the invention is characterized by a high selectivity towards ethane-1-hydroxy-1,1-diphosphonic acid and a perfectly controlled exothermic reaction throughout the whole process.

The free ethane-1-hydroxy-1,1-diphosphonic acid obtained by the method of the present invention can be further neutralized to any desired salt by reacting it with an appropriate base such as for example the hydroxides of alkali metals or the hydroxides of alkaline earth metals, ammonia or amines.

Suitable amines for use in the present invention include aliphatic, cycloaliphatic, heterocyclic and aromatic primary, secondary and tertiary (poly)amines. Among the large numbers of amines that can be used within the scope of the present invention, methylamine, propylamine, 2-propylamine, ethanolamine, propanolamine, n-butylamine, octylamine, ethylene diamine, trimethylene diamine, dimethylamine, methylethanolamine, dibutylamine, trimethylamine, methyl dibutylamine, triethylamine, N,N-dimethyl cyclohexylamine, N-methylpiperidine, aniline, 4-methylaniline and morpholine may be mentioned.

Preferably potassium or sodium hydroxide or ammonia is used to neutralize the diphosphonic acid. The neutralization step can be done at any time after the hydrolysis step.

Because of their multiple commercial applications, sodium, potassium and ammonium salts of ethane-1-hydroxy-1,1-diphosphonic acid are highly desirable.

The chemical reactions of the method according to the invention may be conducted in a batch-wise process.

It may be advantageous to conduct the reaction under pressure; this will speed up the process by increasing the reaction temperature above the acetic acid boiling point.

In another approach the chemical reactions of the method of the invention may be conducted as a continuous process, possibly under autogenous pressure, whereby the reactants are continuously injected into a reaction mixture at a suitable temperature. In the continuous process, as represented in FIG. 5, acetic acid, optionally comprising water, is pumped continuously from a vessel A into a mixing unit C in which it is continuously and intimately mixed with tetraphosphorus hexaoxide, pumped from another vessel B. The reaction mixture leaving the mixing unit C is conveyed continuously to a reactor D or a series of reactors (D, D', D", . . . ) each characterized by a specific temperature and retention time, whereupon the ethane-1-hydroxy-1,1-diphosphonic acid condensates are continuously discharged into a mixing unit C' wherein the condensates are continuously mixed with water and wherein the mixture of condensates and water are continuously conveyed to a reactor E or a series of reactors (E, E', E", . . . ), each standing at a well defined temperature and characterized by a well defined retention time.

Each of the reactors D, (D', D", . . . ) and E (E', E", . . . ) are designed in such a way that they can be operated at pressures between about 0.001 bar (133.3 Pa) and about 15 bar ($1.5*10^6$ Pa). The aqueous solution of ethane-1-hydroxy-1,1-diphosphonic acid leaving the final hydrolyzing reactor E (E', E", . . . ) is then further processed accordingly in working unit F, i.e. dilution with water after removal of excess acetic acid or precipitation from the aqueous solution of step b) comprising the excess of acetic acid. The mixing units C and C' for example are preferably static mixers. The respective liquids are conveyed to the mixing units C and C' using for example and preferably metering pumps guaranteeing specific preset flow rates. The reactors D (D', D", . . . ) and E (E', E", . . . ) are equipped with heat exchanging means capable of managing the reaction temperature in a range between about 20 and about 200° C.

In yet another arrangement, the method can be represented by a semi-continuous setup whereby for example the chemical reactions are conducted continuously whereas the hydrolysis and following processing steps can be conducted batch-wise.

EXAMPLES

The following examples illustrate the invention; they are merely meant to exemplify the present invention but are not destined to limit or otherwise define the scope of the present invention.

Figure 1:
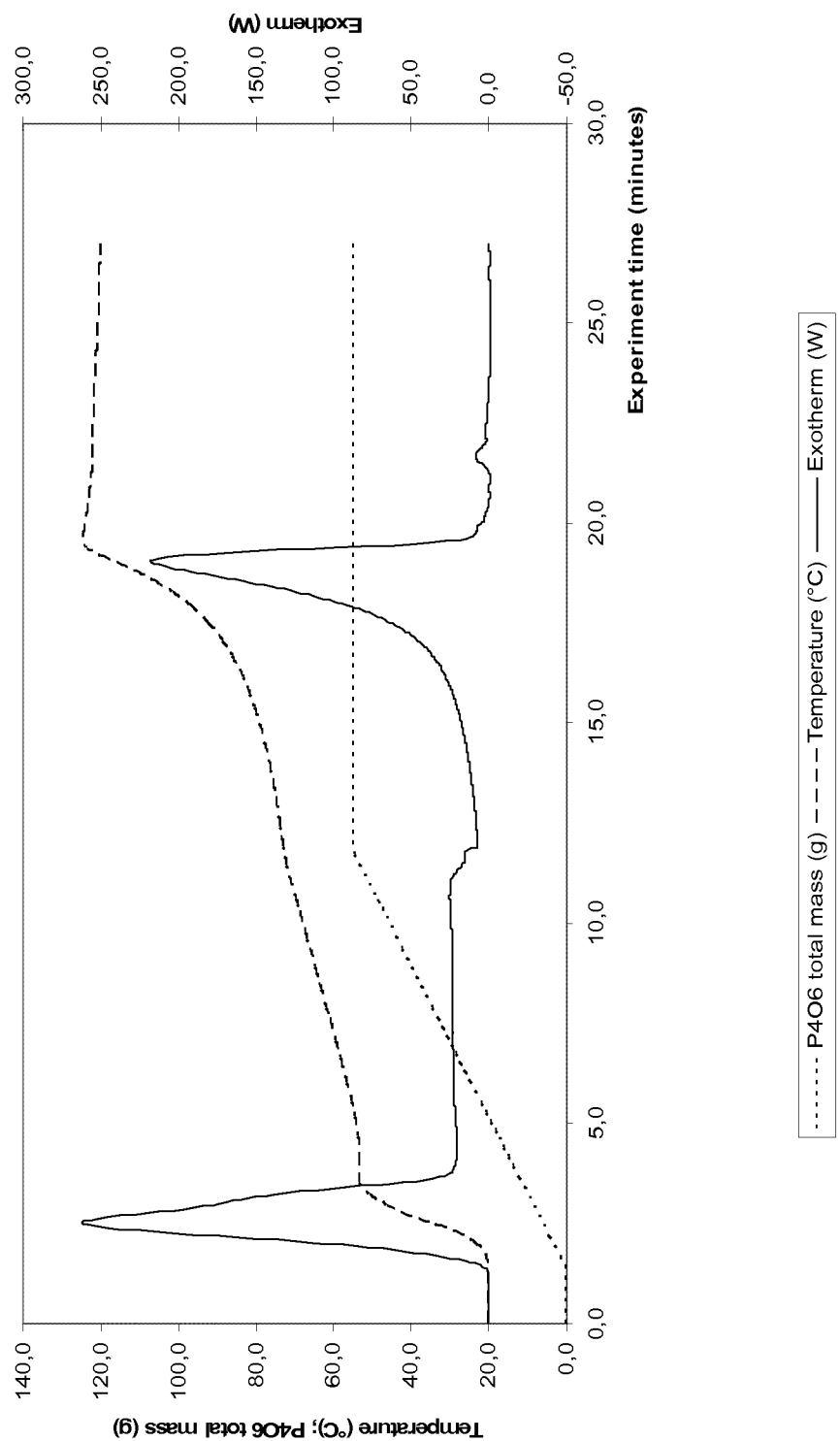
FIG. 1 represents a graph showing the progress of the reaction when applying a method of the comparative example and wherein
  the continuous line represents the exotherm as a function of time;
  the dotted line represents the amount of tetraphosphorus hexaoxide added to the reactor as a function of time;
  the dashed line represents the bulk temperature during the process.
  the left Y axis indicates the reaction medium temperature, in ° C., and the amount of $P_4O_6$, in g, injected in the liquid phase of acetic acid, while the right Y axis indicates the heat generation in W.
Figure 3:
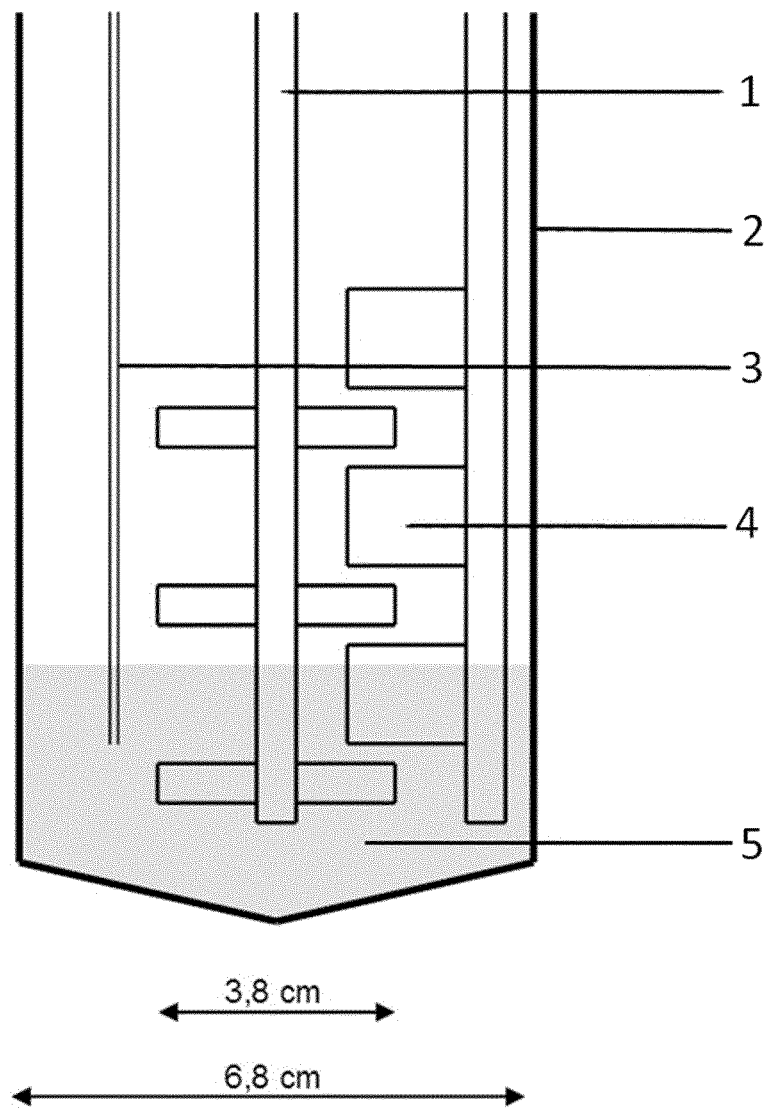
FIG. 3 represents the reactor used in the examples according to the present invention and in the comparative example. The reactor is a 500 ml Mettler-Toledo RC1 calorimeter reactor presenting an internal diameter of 68 mm and a total volume of 500 ml. The reactor is equipped with temperature sensors (not shown in the figure), allowing real time calorimetry, and a stirrer comprising three times four blades with a blade length of 17 mm including the shaft. The lowest stirrer's blades are placed at 5 mm from the bottom of the reactor. Three baffles are placed between the stirrer's blades. The extremity of a 0.5 mm internal diameter injection tubing is placed at 5 mm above the lowest stirrer blades.

Comparative Example 150.1 g (2.5 mole) of glacial acetic acid and 4.5 g (0.25 mole) of water were placed in a 500 ml Mettler-Toledo RC1 calorimeter reactor as represented in FIG. 3, after flushing with nitrogen. The temperature of the acetic acid aqueous solution was then stabilised at 20° C. 55.0 g (0.25 mole) of tetraphosphorus hexaoxide was then added at 4.58 g/min. At the end of the tetraphosphorus hexaoxide addition the bulk temperature was 75° C., the reaction became self heating and an uncontrollable exothermic reaction occurred, bringing the reaction medium to a strong reflux. The reaction mixture was then allowed to further react at 120° C. during 30 minutes. Then 22.25 g of water were added to the reaction mixture and hydrolysis was performed at 140° C. for 60 minutes. The exothermal values and the bulk temperature throughout the tetraphosphorus hexaoxide addition, as recorded from the calorimeter, are represented in FIG. 1. The second exothermic reaction, corresponding to the formation of ethane-1-hydroxy-1,1-diphosphonic acid condensates, occurred after the tetraphosphorus hexaoxide addition was completed. The maximum heat generation for this exotherm was 220 J/s and the amount of energy released after all the tetraphosphorus hexaoxide was added corresponds to 36% of the total exotherm.

As can be seen from FIG. 1 the exotherm is extreme and uncontrollable and only appears after the tetraphosphorus hexaoxide addition is completed. Acyl phosphite and diacyl phosphite are accumulating and once the bulk temperature is high enough, a sudden conversion into ethane-1-hydroxy-1,1-diphosphonic acid condensates takes place. This sudden conversion generates a lot of energy in a short period of time which makes the reaction uncontrollable on an industrial scale; this would generate a major risk of explosion. Ethane-1-hydroxy-1,1-diphosphonic acid was produced with a yield of 95%, as determined by $^{31}P$ NMR analysis.

Examples According to the Invention

Example 1

90.1 g (1.5 mole) of glacial acetic acid and 6.75 g (0.38 mole) of water were placed in a 500 ml Mettler-Toledo RC1 calorimeter reactor as represented in FIG. 3, after flushing with nitrogen.

Figure 2:
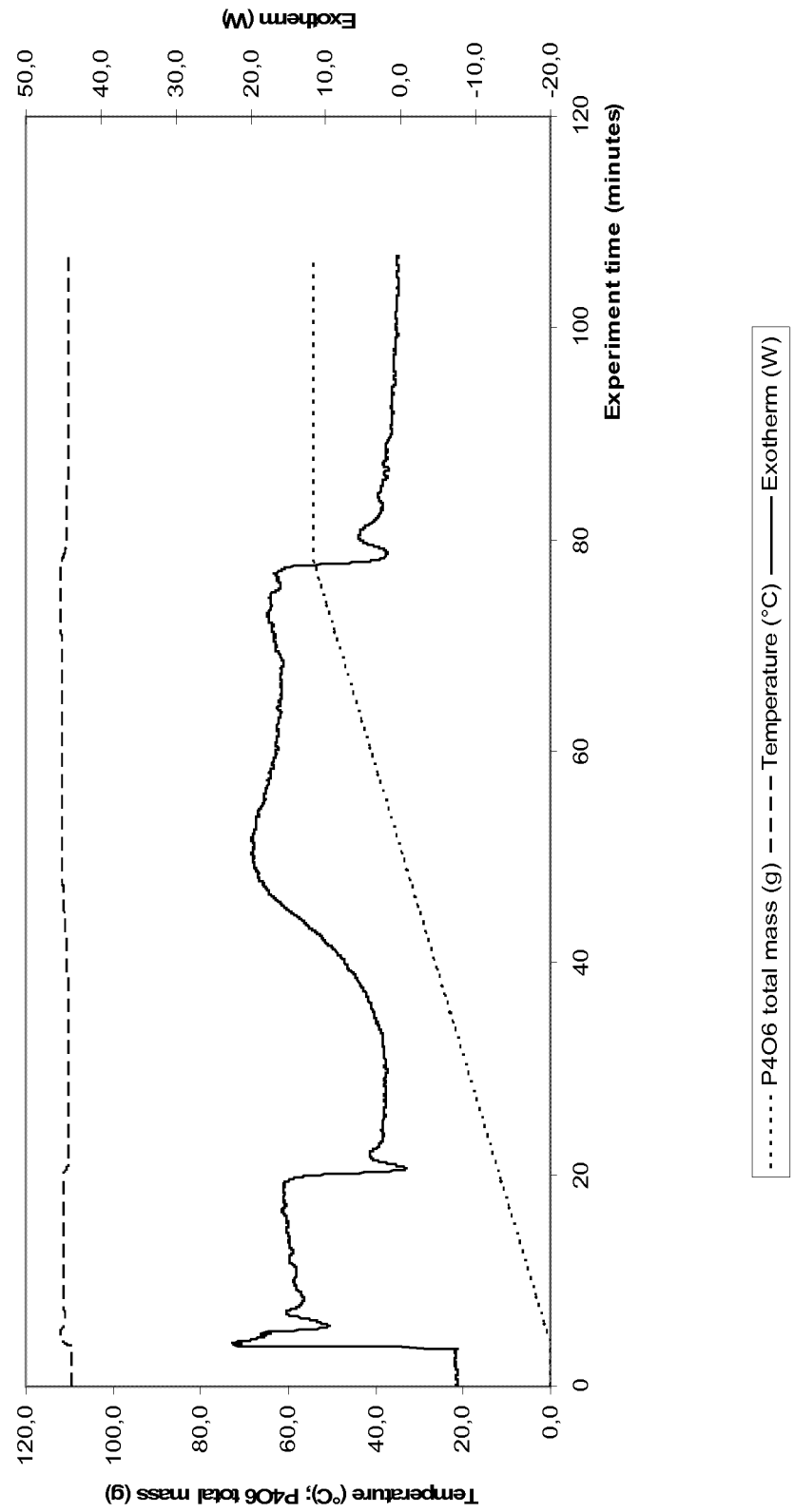
FIG. 2 represents a graph showing the progress of the reaction when applying the method according to the present invention wherein the continuous, dotted, dashed lines and the axes have the same meaning as in FIG. 1.

The acetic acid aqueous solution was heated to 110° C. and stabilised at this value. The stirrer speed was set at 500 rpm (revolutions per minute). 55 g (0.25 mole) of tetraphosphorus hexaoxide were then introduced through the injection tubing at 0.733 g/min, the extremity of the injection tubing being under the surface of the solution. The exothermal values and the bulk temperature throughout the tetraphosphorus hexaoxide addition, as recorded from the calorimeter, are represented in FIG. 2. The mixture was then allowed to further react at 110° C. during 30 minutes in order to complete the reaction. Then 20.25 g of water were added to the reaction mixture and hydrolysis was performed at 140° C. for 60 minutes.

The total amount of energy released was 75 kJ. The maximum energy generation during the formation of ethane-1-hydroxy-1,1-diphosphonic acid condensates was 23 W. The amount of energy released after completion of the tetraphosphorus hexaoxide addition corresponds to 5% of the total exotherm. These values clearly demonstrate that there is a very limited accumulation of energy in this process.

As can be seen from FIG. 2, the exotherm is moderate and controllable throughout the tetraphosphorus hexaoxide addition. The heat generation can be instantly completely stopped by the interruption of the tetraphosphorus hexaoxide addition. The conversion of acyl phosphite and diacyl phosphite into ethane-1-hydroxy-1,1-diphosphonic acid condensates happens on a substantial continuous basis during the tetraphosphorus hexaoxide addition. No extreme exotherm is observed after the completion of the tetraphosphorus hexaoxide addition.

Ethane-1-hydroxy-1,1-diphosphonic acid was produced with a yield of 94%, as determined by $^{31}P$ NMR analysis.

Example 2

In a three-necked round-bottom flask, equipped with a mechanical stirrer, a reflux condenser and an injection tubing for $P_4O_6$ addition as in FIG. 3, were charged, under nitrogen atmosphere, 150.1 g (2.5 mole) of glacial acetic acid and 4.5 g (0.25 mole) of water. The acetic acid aqueous solution was heated to 115° C. and stabilised at this value. 55 g (0.25 mole) of $P_4O_6$ were then introduced through the injection tubing at 0.733 g/min, the extremity of the injection tubing being under the surface of the solution. Intensive stirring was applied during all the $P_4O_6$ addition period. The mixture was then allowed to further react at 120° C. during 60 minutes in order to complete the reaction. Then 22.5 g of water were added to the reaction mixture and hydrolysis was performed at 140° C. for 60 minutes. After cooling to 110° C., 30.02 (0.5 mole) of acetic acid were added. The reaction medium was then cooled to 20° C. over 1 hour and kept at this value for 3 hours whereupon crystallization occurs; the extra amount of acetic acid improves the crystallisation. The solid was filtered and dried at 60° C. to yield 186 g (87% yield) of a white crystalline solid which consisted of the monohydrate form of ethane-1-hydroxy-1,1-diphosphonic acid. The acetic acid, recovered from the process, was used in a subsequent synthesis. By recycling the mother liquor, it was possible to increase the yield to 96%.

Example 3

In a three-necked round-bottom flask, equipped with a mechanical stirrer, a reflux condenser and an injection tubing for $P_4O_6$ addition, as in FIG. 3, were charged, under nitrogen atmosphere, 150.1 g (2.5 mole) of glacial acetic acid and 18 g (1.0 mole) of water. The acetic acid aqueous solution was heated to 115° C. and stabilised at this value. 55 g (0.25 mole) of $P_4O_6$ were then introduced through the injection tubing at 0.733 g/min, the extremity of the injection tubing being under the surface of the solution. Intensive stirring was applied during all the $P_4O_6$ addition period. The mixture was then allowed to further react at 120° C. during 60 minutes in order to complete the reaction. Then 9 g of water were added to the reaction mixture and hydrolysis was performed at 140° C. for 60 minutes. Ethane-1-hydroxy-1,1-diphosphonic acid was produced with a yield of 4%, as determined by $^{31}P$ NMR analysis.

Example 4

This example describes the continuous process of the 1-hydroxyethane-1,1-diphosphonic acid synthesis. The reaction was conducted in the system described in FIG. 5.

$P_4O_6$ (0.192 ml/min.) (B) and a 94.68% aqueous solution of acetic acid 0.808 ml/min.) (A) were separately pumped and mixed in T mixer (C). The mixture was fed to reactor (D) which was heated at 150° C. At the outlet of reactor (D), water was added through T mixer (C') at 0.180 ml/min and the reacting medium was directed to reactor (E) which was heated at 150° C. A back pressure regulator was used to obtain a pressure of 20 bar. Thus an aqueous solution of HEDP was collected in (F). Excess of acetic acid was removed batch wise as described in example 2. Ethane-1-hydroxy-1,1-diphosphonic acid was produced with a yield of 97%, as determined by $^{31}$P NMR analysis.

As clearly appears from the examples according to the invention, the gradual addition, at high temperature, of the tetraphosphorus hexaoxide to the aqueous solution of acetic acid is extremely important for controlling the exothermic reaction. The gradual addition at high temperature induces a continuous conversion of the reactants into ethane-1-hydroxy-1,1-diphosphonic acid condensates.

The gradual addition at room temperature, as in the comparative example, results in an accumulation of acyl phosphite and diacyl phosphite, for which the conversion into ethane-1-hydroxy-1,1-diphosphonic acid, once the bulk temperature becomes sufficiently high, is highly exothermic and uncontrollable.

The method according to the present invention thus allows for up-scaling in a safe and controllable way, contrary to the method of the comparative example, which is unusable and unsafe for industrial scale application.

Example 5

Example 5 demonstrates the influence of acetic acid/$P_4O_6$ and water/$P_4O_6$ ratios over the viscosity of the reacting medium. For all reactions, 1.74 moles of $P_4O_6$ were injected in the specified mixture of acetic acid and water at 120° C. and over 60 minutes. The reacting mediums were allowed to further react during 1 hour after the end of $P_4O_6$ addition. At this point, dynamic viscosities were measured at 120° C. with a ReactaVisc 300 "in process" vibrational viscometer from Hydramotion Ltd. Dynamic viscosity values are reported in table 1.

TABLE 1 viscosity in function of $H_2O/P_4O_6$ and $AcOH/P_4O_6$ ratios

| Entry | AcOH/$P_4O_6$ molar ratio | $H_2O/P_4O_6$ molar ratio | Dynamic viscosity (Pa · sec) |
|---|---|---|---|
| 1 | 6 | 1.5 | 0.70 |
| 2 | 5 | 1.5 | 2.90 |
| 3 | 6 | 1.4 | 0.97 |
| 4 | 5.5 | 1.5 | 1.10 |
| 5 | 4.75 | 1.5 | 28.50 |
| 6 | 10 | 0 | 1.45 |
| 7 | 15 | 0 | 0.35 |

Viscosity values observed with a $H_2O/P_4O_6$ ratio of 1.5 were extrapolated till 60 Pa·s in order to get an approximate value of the minimum amount of acetic acid allowing the reacting medium to be efficiently mixed. As shown in FIG. 6, viscosity strongly increases for AcOH/$P_4O_6$ ratios of about 5 and less.

Example 5 clearly demonstrates that the amount of acetic acid and water have a very significant impact on the viscosity of the reacting medium. Selecting an optimal ratio of acetic acid and water allows for carrying out the reaction at a manageable viscosity.

The invention claimed is:

1. A method for the production of ethane-1-hydroxy-1,1-diphosphonic acid or its salts, under controlled thermal conditions, comprising the steps of:
   a) forming a reaction mixture by gradually injecting tetraphosphorus hexaoxide, under optimal mixing conditions, below the surface of a liquid phase comprising acetic acid, while controlling the temperature of the reaction mixture in the range of from 60° C. to 200° C., wherein said reaction mixture comprises a molar ratio of acetic acid to tetraphosphorus hexaoxide comprised between 4 and 15, selected in such a way that the viscosity of the reaction mixture enables said optimal mixing conditions, the gradual injection leading to the formation of ethane-1-hydroxy-1,1-diphosphonic acid condensates,
   b) hydrolyzing the ethane-1-hydroxy-1,1-diphosphonic acid condensates of the reaction mixture of step a) by adding water, wherein the molar ratio of water to tetraphosphorus hexaoxide, added in step a) is 2 or more, and maintaining the reaction mixture at a temperature comprised between 100° C. and 200° C. to obtain an aqueous solution comprising the ethane-1-hydroxy-1,1-diphosphonic acid.

2. The method according to claim 1 wherein the temperature range of the reaction mixture of step a) is achieved through an initial tetraphosphorus hexaoxide injection step or through a preheating of the liquid phase comprising acetic acid before starting the gradual injection of tetraphosphorus hexaoxide below the surface of said liquid phase.

3. The method according to claim 1, wherein the reaction mixture of step a) is kept at a temperature of 60° C. or more for 5 minutes or more after the completion of the tetraphosphorus hexaoxide addition.

4. The method according to claim 1, wherein the viscosity of the reaction mixture of step a) is 10 Pa·s or less at the temperature of the reaction mixture, comprised between 60° C. and 200° C., throughout the complete duration of step a).

5. The method according to claim 1, wherein the liquid phase comprising acetic acid comprises water, forming an aqueous solution of acetic acid, wherein the molar ratio of water of said aqueous solution to the total amount of tetraphosphorus hexaoxide, added in step a) is comprised between 0.007 and 3.0.

6. The method according to claim 1, comprising the further steps of:
   distilling the excess of acetic acid from the aqueous solution of step b) and adjusting the water content to obtain an aqueous solution comprising ethane-1-hydroxy-1,1-diphosphonic acid, or
   cooling the aqueous solution of step b) to obtain a precipitate of ethane-1-hydroxy-1,1-diphosphonic acid and optionally isolating the precipitate to obtain solid ethane-1-hydroxy-1,1-diphosphonic acid.

7. The method according to claim 1 comprising the further step of neutralizing ethane-1-hydroxy-1,1-diphosphonic acid through the addition of a base selected from the group consisting of hydroxides of alkali metals, hydroxides of alkaline earth metals, ammonia and amines, to form the corresponding salt.

8. The method according to claim 1, wherein the molar ratio of acetic acid to the total amount of tetraphosphorus hexaoxide added in step a) is comprised between 4 and 15.

9. The method according to claim 1, wherein in step a) the tetraphosphorus hexaoxide is gradually injected in the liquid phase (below the surface) of acetic acid or of the aqueous solution of acetic acid for a period of time comprised between 5 minutes and 5 hours.

10. The method according to claim 1, wherein the reaction mixture of step a) is heated to a temperature comprised between 60° C. and 200° C. and is maintained at that temperature throughout the tetraphosphorus hexaoxide addition step.

11. The method according to claim 1, wherein the reaction mixture of step a) is maintained at a temperature comprised between 90° C. and 200° C. for a period of time comprised between 5 minutes and 2 hours after the completion of the tetraphosphorus hexaoxide addition.

12. The method according to claim 1, wherein the molar ratio of water added in step b) to the total amount of tetraphosphorus hexaoxide added in step a) is between 2 and 6.

13. The method according to claim 1, wherein step b) is maintained at a temperature comprised between 100° C. and 170° C., for a period of time comprised between 5 minutes and 4 hours.

14. The method according to claim 6, wherein the excess of acetic acid is distilled in step b) by steam injection.

15. The method according to claim 6, wherein the aqueous solution of step b) is cooled to a temperature comprised between 15° C. and 40° C. to form a precipitate of ethane-1-hydroxy-1,1-diphosphonic acid.

16. The method according to claim 6, wherein the excess of acetic acid is recovered and reused preferably in step a) and step b) of the method.

17. The method according to claim 1, wherein the ethane-1-hydroxy-1,1-diphosphonic acid is obtained in a batch process.

* * * * *